United States Patent [19]

Frey

[11] Patent Number: 4,528,702
[45] Date of Patent: Jul. 16, 1985

[54] JOINT ENDOPROSTHESIS

[75] Inventor: Otto Frey, Winterthur, Switzerland

[73] Assignee: Sulzer Brothers Limited, Winterthur, Switzerland

[21] Appl. No.: 539,565

[22] Filed: Oct. 6, 1983

[30] Foreign Application Priority Data

Oct. 15, 1982 [CH] Switzerland .................. 6018/82

[51] Int. Cl.³ ........................... A61F 1/04; A61F 5/04
[52] U.S. Cl. ..................................... 623/23; 623/18; 128/92 C; 128/92 CA
[58] Field of Search ................. 3/1.912, 1.913; 128/92 C, 92 CA

[56] References Cited

U.S. PATENT DOCUMENTS

| 3,074,292 | 1/1963 | Polmon ................... 29/523 |
| 3,685,058 | 8/1972 | Tronzo ................... 3/1.912 |
| 3,916,451 | 11/1975 | Beuechel et al. ....... 3/1.912 |
| 4,012,795 | 3/1977 | Doore et al. ........... 128/92 CA |

FOREIGN PATENT DOCUMENTS

| 0024442 | 3/1981 | European Pat. Off. ........ 3/1.912 |
| 2524923 | 11/1976 | Fed. Rep. of Germany ...... 3/1.912 |
| 720092 | 12/1954 | United Kingdom ........... 128/92 CA |

Primary Examiner—Richard J. Apley
Assistant Examiner—David J. Isabella
Attorney, Agent, or Firm—Kenyon & Kenyon

[57] ABSTRACT

The conical pin end of the male endoprosthesis part is provided with a deformable surface while the conically recessed articular ball is provided with inwardly directed lugs for penetrating into the deformable surface during mounting on the pin end. The lugs have a maximum height of 0.5 millimeters and a maximum width of three millimeters. The deformable pin surface may be formed by a screw thread, a plurality of circumferential grooves of wavy configuration or a plurality of circumferential ribs.

12 Claims, 5 Drawing Figures

JOINT ENDOPROSTHESIS

This invention relates to a joint prosthesis and, more particularly, to a joint endoprosthesis for a femur head.

As is known, endoprostheses have frequently been made with an articular ball, for example for a femur head prosthesis, joined to an anchoring shank by means of a cone plug connection. For example, as described in German O.S. No. 2548 077 it has been known to mount an articular ball onto a conical pin of an anchoring shank in a self-locking manner. However, in the case of relatively large articular balls which are subject to increased torsion moments, for example as used for the so-called fracture prosthesis, undesirable relative rotations will often occur between the articular ball and the pin after implantation.

It has also been known from Swiss Pat. No. 507,704 and German PS No. 22 20 304 to use a conical plug connection to fasten an articular ball on a pin where the pin axis does not coincide with the axis of symmetry of the articular ball. This permits the position of the articular ball relative to the femur axis to be approximated to the individual differences in the skeletal build of the various patients. However, for such prosthesis having an "oblique" position of the two axes, the articular ball must be prevented from becoming twisted relative to the pin during the "life" of the prosthesis. For this reason, it has been known to provide the base of the pin with an anti-twist construction, for example in the form of ribs, lugs, teeth or the like to engage in matching radial grooves in the surface of a female conical surface in the articular ball. However, apart from the fact that the making of the grooves in the conical female surface requires much additional cost, the anti-twist constructions have the disadvantage that they do not permit a continuous adjustment of the articular ball relative to the pin. Instead, these constructions only permit a relative rotation corresponding to the number of grooves in order to fix the ball on the pin. Hence, the operating surgeon must consider the specific angular position between the articular ball and pin during an operation.

Accordingly, it is an object of the invention to provide a means by which an articular ball can be fastened on a pin by an operating surgeon without consideration of the specific angular position between the pin and articular ball.

It is another object of the invention to be able to continuously adjust the position of an articular ball to a pin on which the ball is to be mounted during an operation.

It is another object of the invention to provide a joint endoprosthesis which can be manufactured in a simple manner to protect against relative twisting of the joints parts on each other.

Briefly, the invention provides a joint endoprosthesis which is comprised of a first part having a conical end with a deformable surface and a second part which includes a conical recess receiving the conical end of the first part. In addition, the second part is provided with at least one inwardly projecting lug at an inner end of the conical recess which is able to penetrate into the deformable surface of the first part in order to prevent a relative turning between the two parts.

The joint prosthesis may be constructed, for example as a femur head prosthesis. To this end, the first part of the joint includes an anchoring shank at one end for implanting in a bone while the conical end extends from an opposite end in the form of a pin. The second part is constructed in the form of an articular ball having an internal conical recess for mounting on the conical pin.

As the articular ball is placed on and driven in, or pressed in, the lug which may be in the form of a spike or a cylindrical or spherical projection penetrates into the deformable surface on the pin and thus brings about a desired antitwist protection. As the possible shearing forces that might cause a twisting of the ball are relatively small, a single lug, in principle, should be sufficient to impart the anti-twist protection. Of course, several lugs may be distributed over the circumference of the conical recess of the articular ball in order to protect against larger shearing forces.

Since the conical pin of the first part has a uniform surface about the entire circumference without any privileged areas, the recessed second part, i.e. the articular ball, can be placed on and secured in any desired position of the lug relative to the circumference of the pin. Thus, the operating surgeon need not pay attention to a specific position of the ball relative to the pin. Further, for an "oblique" axes situation, a continuous adjustability exists.

As described, the lug of the recessed joint part is able to penetrate into the structure of the surface of the pin. Naturally, the force required must not be excessive in order to avoid damage to either part. Accordingly, it is advantageous if the maximum height of the lug is 0.5 millimeters with a maximum width of 3 millimeters.

The anti-twist construction is applicable to all materials which are customarily used for the manufacture of a prosthesis, provided the material for the articular ball is less deformable than the surface regions of the pin. Naturally, the deformability of the surfaces of the pin may, if desired, be produced by the selection of a softer material for the conical pin.

The deformable surface on the pin may be formed in various manners. For example, the deformable surface may be formed by a screw thread, by a plurality of circumferential grooves of wavy configuration or by a plurality of circumferential ribs. In addition, the surface may have circumferential recesses of decreasing depth in a direction towards the anchoring shank in order to implant greater resistance to deformation in that direction.

These and other objects and advantages of the invention will become more apparent from the following description taken in conjunction with the accompanying drawings wherein.

Figure 1:
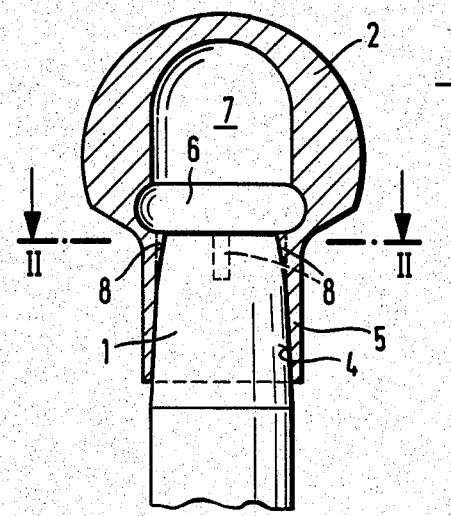
FIG. 1 illustrates a longitudinal sectional view through a joint endoprosthesis constructed in accordance with the invention.

Referring to FIG. 1, the joint endoprosthesis includes a male part having an anchoring shank (shown in part) for implanting in a femur bone and a pin 1 which forms a conical end opposite the shank. In addition, the prosthesis has a female part in the form of an articular ball 2 which is secured on the pin 1 via a self-locking coical plug connection. As indicated, the ball 2 has a neck-type projection 5 which is made in one piece with the ball 2 and in which a conical recess 4 is formed for receiving the conical end of the pin 1. The ball 2 also has an undercut 6 which is contiguous to the conical recess 4 and an internal cavity 7 which is spaced from the undercut 6. Of note, the undercut 6 is necessary for the production of the conical recess 4 while the cavity 7 serves to save weight or, in the case of a cast or poured articular ball 2, is necessary for the casting operation.

The pin 1 is further provided with a deformable surface 3 which is sufficient to increase the deformability of the pin 1 relative to the ball 2. In addition, the ball 2 is provided with a plurality of inwardly projecting lugs 8 at the tapered end of the recess 4. These lugs 8 are distributed over the periphery of the recess 4 and are formed so as to penetrate into the deformable surface 3 of the pin 1 upon pressing on or hammering on of the ball 2 onto the pin 1. These lugs thus serve to provide an anti-twist protection against a relative twisting between the ball 2 and the pin 1.

Figure 2:
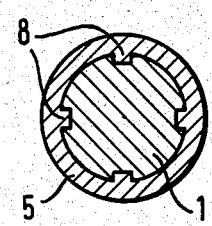
FIG. 2 illustrates a view taken on line II—II of FIG. 1.

Referring to FIG. 2, each lug 8 may have a maximum height of 0.5 millimeters and a maximum width of 3 millimeters.

Figure 3:
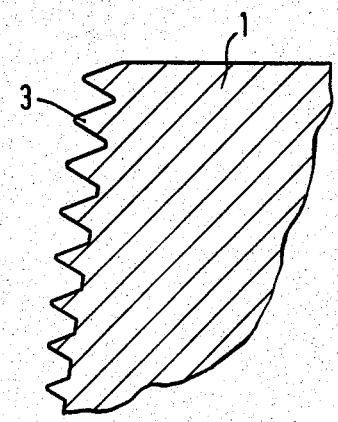
FIG. 3 illustrates an enlarged detailed view of the end of a pin having a deformable surface formed by a screw thread.
Figure 4:
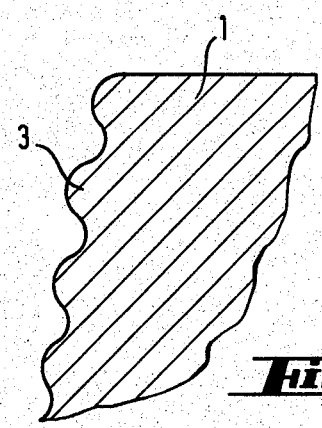
FIG. 4 illustrates a modified deformable surface formed by circumferential grooves of wavy configuration.
Figure 5:
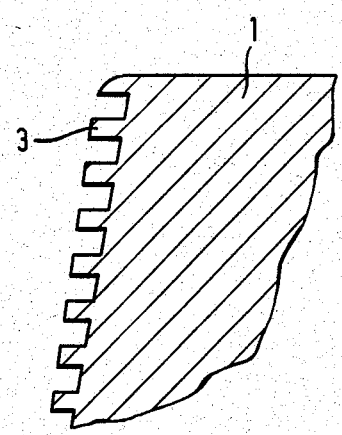
FIG. 5 illustrates a further modified deformable surface formed by circumferential ribs in accordance with the invention.

Referring to FIG. 3, the surface 3 of the pin 1 may be formed by means of a screw thread. Alternatively, as shown in FIG. 4, the deformable surface 3 may be formed by a plurality of circumferential grooves of wavy configuration or, as shown in FIG. 5, by a plurality of circumferential ribs. Advantageously, the deformable surface 3 may be formed of a plurality of circumferential recesses of decreasing depth in a direction towards the anchoring shank of the male part in order to impart greater resistance to deformation in this direction. Thus, the deformability of the conical end of the pin 1 may decrease inwardly so that the pin offers greater resistance to deformation as the articular ball 2 is moved onto the pin 1 a farther distance.

Of note, the conicity of the recess 4, while being adapted to the conicity of the end of the pin 1, need not necessarily coincide with the coinicity of the pin 1.

The invention thus provides an endoprosthesis with a relatively simple means for resisting relative rotation between an articular ball and a pin end of an anchoring shank.

What is claimed is:

1. A joint endoprosthesis comprising
a first part including an anchoring shank for implanting in a bone and a conical end opposite said shank having a plurality of ribs forming a deformable surface thereon; and
a second part including a conical recess receiving said conical end of said first part and at least one projecting lug formed on a surface solely at an inner end of said recess and projecting inwardly into said recess, said lug being of harder material than said first part thereby penetrating into and deforming said ribs of said deformable surface of said first part to prevent relative rotation between said parts.

2. A joint endoprosthesis as set forth in claim 1 wherein said lug has a maximum height of 0.5 millimeters and a maximum width of 3 millimeters.

3. A joint endoprosthesis as set forth in claim 1 wherein said second part is an articular ball for a femur head prosthesis.

4. A joint endoprosthesis as set forth in claim 3 wherein said ball has an internal cavity spaced from said first part and an undercut between said cavity and said conical recess.

5. A joint endoprosthesis as set forth in claim 1 wherein said conical end of said first part has a screw thread forming said deformable surface.

6. A joint endoprosthesis as set forth in claim 1 wherein said conical end of said first part has a plurality of circumferential ribs of wavy configuration forming said deformable surface.

7. A joint endoprosthesis as set forth in claim 1 wherein said conical end of said first part has a plurality of circumferential ribs forming said deformable surface.

8. A joint endoprosthesis as set forth in claim 1 wherein said conical end of said first part has a plurality of circumferential recesses of decreasing depth in a direction towards said anchoring shank to impart greater resistance to deformation in said direction.

9. A joint prosthesis comprising
a first part having a conical end with a plurality of ribs forming a deformable surface thereon; and
a second part including a conical recess receiving said conical end of said first part and at least one projecting lug formed on a surface solely at an inner end of said recess and projecting inwardly into said recess, said lug being harder than said first part thereby penetrating into and deforming said ribs of said deformable surface of said first part to prevent relative rotation between said parts.

10. A joint prosthesis as set forth in claim 9 having a plurality of said lugs embedded in said conical end of said first part.

11. A joint prosthesis as set forth in claim 9 wherein said lug has a maximum height of 0.5 millimeters and a maximum width of 3 millimeters.

12. A joint prosthesis as set forth in claim 11 wherein said lug is of cylindrical shape.

* * * * *

UNITED STATES PATENT AND TRADEMARK OFFICE
CERTIFICATE OF CORRECTION

PATENT NO. : 4,528,702
DATED : July 16, 1985
INVENTOR(S) : Otto Frey

It is certified that error appears in the above-identified patent and that said Letters Patent is hereby corrected as shown below:

Column 3, line 1 change "coical" to -conical-

Signed and Sealed this

Fourteenth Day of January 1986

[SEAL]

*Attest:*

DONALD J. QUIGG

*Attesting Officer*     *Commissioner of Patents and Trademarks*